| | | | |
|---|---|---|---|
| (12) | United States Patent | (10) Patent No.: | US 7,529,577 B2 |
| | Jensen et al. | (45) Date of Patent: | May 5, 2009 |

(54) METHOD AND APPARATUS FOR LOCATING FOREIGN OBJECTS IN THE EAR CANAL

(75) Inventors: Preben Damgård Jensen, Birkerød (DK); Tom Olesen, Gørløse (DK)

(73) Assignee: Oticon A/S, Smørum (DK)

( * ) Notice: Subject to any disclaimer, the term of this patent is extended or adjusted under 35 U.S.C. 154(b) by 611 days.

(21) Appl. No.: 10/476,581

(22) PCT Filed: May 8, 2002

(86) PCT No.: PCT/DK02/00303

§ 371 (c)(1),
(2), (4) Date: Nov. 19, 2003

(87) PCT Pub. No.: WO02/091914

PCT Pub. Date: Nov. 21, 2002

(65) Prior Publication Data

US 2004/0158157 A1 Aug. 12, 2004

(30) Foreign Application Priority Data

May 17, 2001 (DK) .............................. 2001 00785

(51) Int. Cl.
*A61B 6/00* (2006.01)
(52) U.S. Cl. ................. 600/478; 356/241.6; 356/241.1; 600/476; 600/477; 600/117
(58) Field of Classification Search ................. 600/407, 600/473, 184, 160, 424; 606/130; 356/241.1, 356/241.6

See application file for complete search history.

(56) References Cited

U.S. PATENT DOCUMENTS

| | | | |
|---|---|---|---|
| 5,004,339 A | 4/1991 | Pryor et al. | |
| 5,847,832 A | 12/1998 | Liskow et al. | |
| 5,916,150 A * | 6/1999 | Sillman | ....................... 600/184 |
| 6,017,353 A * | 1/2000 | Rankins | ....................... 606/162 |
| 6,141,577 A | 10/2000 | Rolland et al. | |
| 6,577,891 B1 | 6/2003 | Jaross et al. | |

FOREIGN PATENT DOCUMENTS

| | | |
|---|---|---|
| EP | 0352952 | 1/1990 |
| WO | 0034739 | 6/2000 |
| WO | 0216867 | 2/2002 |

OTHER PUBLICATIONS

Patent Abstracts of Japan, vol. 1998, No. 1, Jan. 30, 1998 of JP 09 248281, Olympus Optical Co. Ltd., Sep. 22, 1997.
English translation of DE 19750698.

* cited by examiner

*Primary Examiner*—Brian L. Casler
*Assistant Examiner*—Sanjay Cattungal
(74) *Attorney, Agent, or Firm*—Dykema Gossett PLLC

(57) ABSTRACT

The invention concerns a method for locating foreign objects on the internal surface of ear and ear canal whereby a probe having a light emitting distal portion is inserted into the ear canal, the method further comprising the steps of:—directing light from the distal portion of the probe to illuminate at least one point or the internal circumferential surface of the ear and/or ear canal,—receiving the light reflected from the illuminated surface, and directing the received light to at least one light sensitive element to generate an output,—analyzing the output with respect to spectral composition in order to identify foreign objects. The invention also relates to an apparatus for locating foreign objects on the internal surface of ear and ear canal.

11 Claims, 3 Drawing Sheets

METHOD AND APPARATUS FOR LOCATING FOREIGN OBJECTS IN THE EAR CANAL

AREA OF THE INVENTION

The invention relates to a method and an apparatus for locating foreign objects in the ear canal. The method and the apparatus are used in the process of gaining data for mapping the internal surface of the ear and ear canal, so that a 3-dimensional data or digital model of the internal surface of the ear and ear canal is obtained. Such a 3-dimension model can be used to produce a shell, which has the exact shape of the canal and the shell may form the basis for an ITE or CIC hearing aid. Also earmoulds or shells for other purposes such as a hearing protection or for headsets may be produced from the data model. The shell can be produced on the basis of the data model in different ways, such as by recent developed rapid prototyping methods or by well known machining, e.g. in a CNC machining center.

Today hearing aid shells are produced on the basis of an ear impression taken by introducing a semi-fluent material into the ear canal, which is left to cure in the ear. After curing the semi-fluent material becomes elastic and coherent and is pulled out of the ear canal in one piece. A shell is produced on the basis of this ear impression. Having the ear impression taken is associated with discomfort for the patient, and in many cases the resulting shell does not fit the canal very well. Therefor a method and a device is sought whereby a hearing aid shell may be produced without the necessity of taking the ear impression. Further it is important that foreign objects located in the ear or ear canal does not corrupt the acquisition of the data used to generate the data model.

The advantage of having a data model of the ear canal is that the production of the shell can take place at any location, which means that hearing aid manufactures may produce the shells at a central production facility. Uniform quality can then be ensured. Further the data model may be transmitted either as it is obtained or right thereafter for evaluation at a production facility. Thereby a data model of the hearing aid, which may be realized based on the dimensions and shape of the canal may be generated. The data model of the hearing aid can be transmitted back to the end user for visual evaluation.

BACKGROUND OF THE INVENTION

In the following documents some of the above problems are addressed, but no satisfactory solutions are presented.

U.S. Pat. No. 5,487,012 discloses a method for computer controlled production of an adaptive earpiece comprising at least one part, which is individually matched to the contours of an auditory canal. The method comprise the steps of tracing of the contours of the auditory canal to obtain contour data, digitization of the contour data and storage of the digitized values, converting the digitized values into a multi-dimensional computer model of the external contours of the adaptive earpiece and producing the earpiece on the basis of the computer model. The patent mentions that the tracing of the internal contours of the ear canal may be performed using ultra sound. The document further discloses a method for tracking the ear canal based on the use of an ear impression, but such a method would not resolve the problems relating to the usual way of producing shells as described above.

U.S. Pat. No. 5,056,204. In this document a method for producing a hearing aid, which is worn in the ear is described. The method comprise the steps of initially taking measurements of the inner space of the ear up to the eardrum for use in producing an individual shape of the body member corresponding with the measurements of the inner space of the ear. It is mentioned that the measurement is done by means of a laser. How this actually takes place is not disclosed.

PCT application WO 00/34739 discloses a method for manufacture of a hearing aid shell comprising a motor actuated ultrasonic probe used to acquire the shape data of the ear canal, an image processing computer, which also incorporates the driving electronics for the probe, with an edge detection algorithm used to filter the data. Thereby a digital image file of the three-dimensional topography of the ear canal is obtained. The ultrasonic probe is combined with a fiber optic probe used to monitor the position of the probe within the canal. The fiber optic probe comprises an inner coherent bundle of fibres and an objective lens that relay the image of the canal to a C.C.D. camera and an outer incoherent bundle of fibres that surround the coherent bundle and permits the illumination of the canal by an external light source that is optically coupled to the other end of the incoherent bundle. The position of the probe is determined solely by monitoring the displacement of the probe in one linear direction. Only the possibility of monitoring the motor, which is a step-motor is mentioned for this purpose. The probe is mounted on a stiff rod, and is not capable of following the possible bends of the ear canal. This limits the use of the probe, as many hearing-impaired people especially older people have ear canals with sharp bends.

Various methods and apparatuses for determining the internal properties of internal surfaces have been suggested, however none of these are useful when it comes to mapping the internal surface of a canal of the human body, in order to generate a digital model of the interior wall of the canal.

U.S. Pat. No. 5,004,339 discloses an apparatus for determining a characteristic of the inside surface of a bore comprising:
a guided wave fiber optic element capable of insertion into a bore;
a laser light source for directing light onto the proximal end of said fiber optic element;
means for directing light emanating from the distal end of said fiber optic element onto the inside surface of said bore and for directing light reflected from the inside surface of said bore onto the distal end of said fiber optic element; and
photo detector means capable of generating an output signal dependent upon light incident thereon;
means for directing light emanating from the proximal end of said fiber optic element onto said photo detector means whereby the output signal of said photo detector provides an indication of a characteristic of an inside surface of a bore. The patent further concerns a method for determining a characteristic of the inside surface of a bore using the above apparatus. The method may be employed on a body passage. Obtaining dimensional information concerning a cylindrical surface is mentioned, but not described in detail. Visualization of the bore wall of a sample is described. The sampled and held output of array video data is fed to the y and z axis of a storage video display with the x axis comprised by a pickoff of the movement along the bore length. No system for generating precise information concerning the position and orientation of the distal end of the fiber optic element is mentioned. The means for directing light from the distal end of the optic element onto the inside surface of the bore may be a mirror surface or a lens such as a wide-angle lens. The mirror surface can be designed to focus light on a point of the bore wall surface which is axially forward of the forward most portion of the mirror. This may be used to examine the bottommost portion of a blind bore. The patent does not mention the combined use of a mirror surface and a lens. Also the use of a semi-transparent mirror intended to direct part of the light to the circomferential surface and another part of the light to the surface which is axially forward of the mirror is not mentioned.

U.S. Pat. No. 5,469,245 relates to a method and an apparatus for measuring a three-dimensional position of a surface of a lengthwise object such as a pipe having a uniform cross section from a corresponding two-dimensional observed image of the object surface to measure, for example, the size of a defect in the surface. The patent does not mention systems to determine the exact location and orientation of a probe, which is inserted into the pipe.

U.S. Pat. No. 5,895,927 relates to a method and apparatus for profiling and dimensionalizing an interior cross-sectional portion of a tubular structure. The probe utilizes a disc of unfocused light to illuminate a cross-section of the interior surface and images the illuminated cross-section from the interior surface to a photo detector array, where the image can be evaluated. The photo detector array provides a continuous video signal, which can be fed to a video monitor and to a frame grabber. The resulting array of numbers can be processed by a computer program to find those pixels, which represent the illuminated cross-section, and through this, dimensional (diameter) data may be obtained. The patent does not mention systems for determining the position and orientation of the probe, in order to gain information relating to the length of the tubular structure or relating to possible bends in the tubular structure.

U.S. Pat. No. 6,073,043. This document describes a method and apparatus for determining the position and orientation of a remote object relative to a reference coordinate frame. The method and apparatus includes a plurality of field-generating elements for generating electromagnetic fields and a drive for applying signals to the generating elements. The signals generate a plurality of electromagnetic fields that are distinguishable from one another. The apparatus comprises a remote sensor having one or more field-sensing elements for sensing the fields generated and a processor for processing the outputs of the sensing element(s) into remote object position and orientation relative to the generating element reference coordinate frame. The position and orientation solution is based on the exact formulation of the magnetic field coupling. The system can be used for locating the end of a catheter or endoscope, digitizing objects for computer databases, virtual reality and motion tracking.

SUMMARY OF THE INVENTION

The object of the invention is to provide a method for locating foreign objects on the internal surface of the ear and ear canal of the human body. Foreign objects, which may be located in the ear or ear canal, could cause corruption of acquired data relating to the geometry of the ear canal. By the method of the invention a more accurate data model of the internal surface of the ear and ear canal may be generated. When foreign objects are located, the measurement should stop, and the object be removed, ore the object may be left out of a data model generated of the internal surface of the ear and ear canal.

This is achieved by the method according to claim 1. The invention uses light to locate any foreign objects in the ear or ear canal. The knowledge of the presence of an object may be used to conclude that a precise data model of the ear and ear canal cannot be obtained before the foreign object is removed.

If the location, size and geometry are known, the object may be left out when generating data relating to the canal. In a preferred embodiment the output is therefor analyzed to determine the distance from the probe to the illuminated surface of the canal wall. When the position of the probe is known, such distance data may be used to generate a data model of the ear and ear canal. Thereby possible foreign objects can be left out of the data model, and the surface behind the objects may be generated through ekstrapolation.

The use of light makes it possible to obtain very precise data. The inside of the ear canal need not be touched during measurement, and this is important for two reasons. Firstly because the internal surface of the ear canal is very sensitive and touching thereof is unpleasant for the patient, and secondly the ear canal may deform when touched, and this might disturb the measured distance values and thereby corrupt the obtained data model.

In an embodiment of the method distance data are obtained and recorded while position data concerning the spatial position and rotation of the distal portion of the probe are obtained and recorded during movement of the probe from a first to a second location. Thereby an operator may map a larger coherent area of the internal surface of the ear canal in an easy and straightforward way as the data are recorded during operator controlled motion of the probe.

Preferably the light sensitive element comprises an array of light sensitive elements such as CCD elements.

In a further embodiment the probe has a flexible part and is capable of bending. This has the advantage that the probe is capable of assuming the shape of the ear canal. This makes it possible to insert and retract the probe the full length of the ear canal as the probe continually assumes the shape of the ear canal. The ear canal of especially elderly people may have sharp bends, and by using the invention, the probe may be carefully maneuvered past such bends as data are recorded, and without making impressions in the tissue of the ear canal, which might corrupt the measurements.

Measurements may be performed while moving the probe either towards or away from the tympanic membrane. In an embodiment according to the invention the measurements are performed while moving the probe away from the tympanic membrane. The operator may then place the probe deep in the ear, while taking care that the tympanic membrane is not touched, and then start the measurements and pull the probe gently out of the ear while taking the measurements. The probe may either be pulled out by hand, or a guiding mechanism may be provided, to make sure that the probe is moved at a uniform speed.

A further object of the invention is to provide an apparatus for obtaining geometrical data relating to the internal surface of the ear and ear canal of the human body in order to be able to generate an exact model of the internal surface of the ear and ear canal.

A very simple apparatus for locating objects on the internal surface of the ear and ear anal is achieved by the apparatus comprising:

- a probe having a rod part with a proximal end and a distal portion and comprising at least one light guide and a light source at the proximal end of the light guide,
- a light emitting distal portion insertable into the ear canal and having means for directing light from the distal end of the light guide onto at least one point of an internal circumferential surface area of the ear and/or ear canal,
- means for receiving the light reflected from the illuminated area, and means for directing the received light to at least one light sensitive element to generate an output, means for analyzing the output with respect to the spectral composition of the light received at the light sensitive element to locate any foreign objects.

In a preferred embodiment the output is also analyzed to determine the distance to the illuminated area. When the position of the probe is known, the data may be used to generate a data model of the geometry of the internal surface of the canal. In this model, the identified foreign objects can be left out, and the surface data relating to the surface behind the foreign object is generated through interpolation.

Focusing means in the form of a lens may be inserted in the light path between the light guides and the mirror, to obtain a focused light beam directed towards the internal canal surface.

Preferably the light sensitive element in the apparatus comprises an array of light sensitive elements such as CCD elements.

In and advantageous embodiment the light path between the second mirror surface and the CCD element comprises an image guide between the distal end and the proximal end of the probe, and the CCD element is arranged at the proximal end of the probe, and receives the light emitting from the image guide. A flexible image guide is chosen, so that it may bend along with the probe to follow the bends of the ear canal. The CCD element is arranged at the proximal end of the image guide, away from the ear of the patient during measurement. The advantage is here that no severe space restrictions exist, and the most suitable CCD element may be chosen along with possible lenses, without regard to size.

In an advantageous embodiment the light source generates light containing wavelengths within a first wavelength range and a second wavelength range, and at least the first mirror surface is arranged on a transparent body, whereby the mirror surface reflects light in a first wavelength range and is transparent to light in a second wavelength range and transmits the light in the second wavelength range and whereby the light in the second wavelength range is directed to the area in front of the distal portion of the probe, and the light reflected from any objects in this area is directed through the transparent body and guided towards the CCD element. By this arrangement it becomes possible to receive two images at the CCD element, one of the circumference of the ear canal, and one of the environment in front of the tip of the probe. The two images will be in each their wavelength range and may then be captured by one and the same CCD element.

The mirror surface preferably comprises a coating on the transparent body.

Preferably the CCD element is sensitive to light in both the first and the second wavelength range and the first or the second sensitive wavelength range may be selected. Thereby one and the same CCD element may be used to capture pictures from the circumference and from the front of the probe.

Control of the light received at the CCD may be achieved by controlling the light input to the light guide. When the area in front of the probe is to be illuminated, light in the second wavelength range is inputted to the light guide, and when the circumference is to be illuminated, light in the first wavelength is used. Control of the light input to the light guide may be obtained through control of the light source or by the use of filters.

In another embodiment the probe comprises two CCD elements sensitive to each their wavelength range, whereby a mirror having a semitransparent coating is arranged such that one of the CCD elements receives the light from the circumference and the other CD element receives the light reflected from the area in front of the distal portion of the robe. In this case the two pictures are available at all times at the two CCD elements.

DESCRIPTION OF A PREFERRED EMBODIMENT

Figure 1:
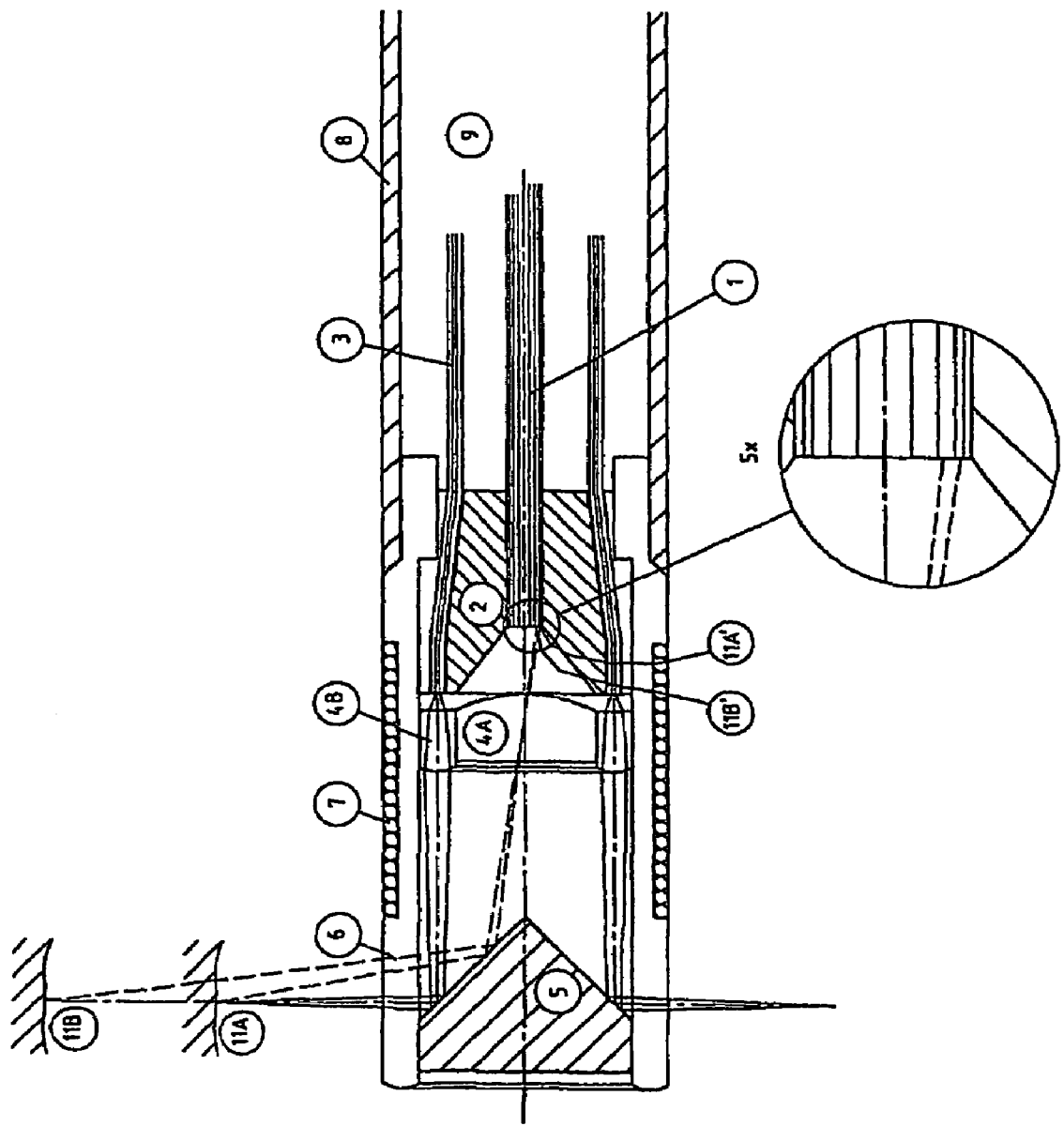
FIG. 1 is a sectional view of a the distal end of a probe showing the light path for determining the distance to the inside wall of a canal.

The probe shown in FIG. 1 has a distal light emitting portion and a rod portion 9, which connects the distal portion to a proximal part (not shown). The rod portion 9 comprises a flexible pipe 8 and a set of light guides 3 and an image guide 1. The image guide 1 is placed centrally in the pipe 8, and the light guides 3 are arranged between the pipe 8 and the image guide 1. Near the tip of the probe the light guides 3 are fastened between an inner bushing 2 and an outer tube 6. An annular lens 4B is arranged at the bushing 2 to capture the light emitting from the light guides 3, in order to focus said light. The focused light beam is directed to a first portion of a mirror 5 mounted at the tip of the tube 6. The first portion of the mirror 5 has a circumferential conical plane with a top angle of 45°. Thereby the focused light beam emitted from the lens 4B will be directed in a right angel away from the longitudinal axis of the probe, and towards the surrounding canal wall 11. The tip portion of the tube 6 is made of a transparent material, so that the light may be transmitted freely through the tube wall.

In FIG. 1 the wall 11 is shown as an example in a first distance at 11A near the tip of the probe and in a second distance 11B farther away from the tip of the probe. Light reflected from the wall at 11A of the canal will enter the tube 6 and be reflected from a second portion of the mirror 5 and enter a second lens 4A. From the lens 4A the light is directed towards the surface of the image guide 1. If light is reflected from a wall part 11B farther away from the probe, it will also be directed towards the surface of the image guide 1, but as can be seen in the enlarged section labeled "5×" this light enters the image guide 1 closer to the center thereof. The second portion of the mirror 5 has a circumferential conical plane, but with a top angle which may differ from 45°.

The image received on the surface of the image guide 1 is transmitted through the image guide 1, and will appear at the other end thereof. Here the image is captured by a CCD array (not shown). The signal from the CCD is transferred to a signal processing unit for further processing in order to calculate the distance from the probe to the canal wall. This is done by a triangulation method well known in the art.

In stead of an image guide, it is possible to arrange the CCD array at the distal end of the probe, such that the reflected light is captured at the distal end of the probe. This is a simpler construction, but it requires a CCD element, which is small enough to be mounted at the tip of the probe, which is going to enter the ear canal. The signal from the CCD element in this case is carried in the usual way by wire back to the proximal end of the probe to be analyzed as described to determine the distance to the wall of the ear canal.

In the preferred embodiment a focused light beam is directed towards the wall of the canal, but also unfocused light may be used. The advantage of using focused light is that the focused light provides better contrast and this result in a more precise detection of the distance between the probe and the canal wall.

A single light guide may be used for both directing light to the tip of the probe and for transmitting the reflected light back to the CCD element. But this requires a beamsplitter, and has the disadvantage of a reduced signal to noise ratio, and therefore the separate light guides are preferred.

Figure 2:
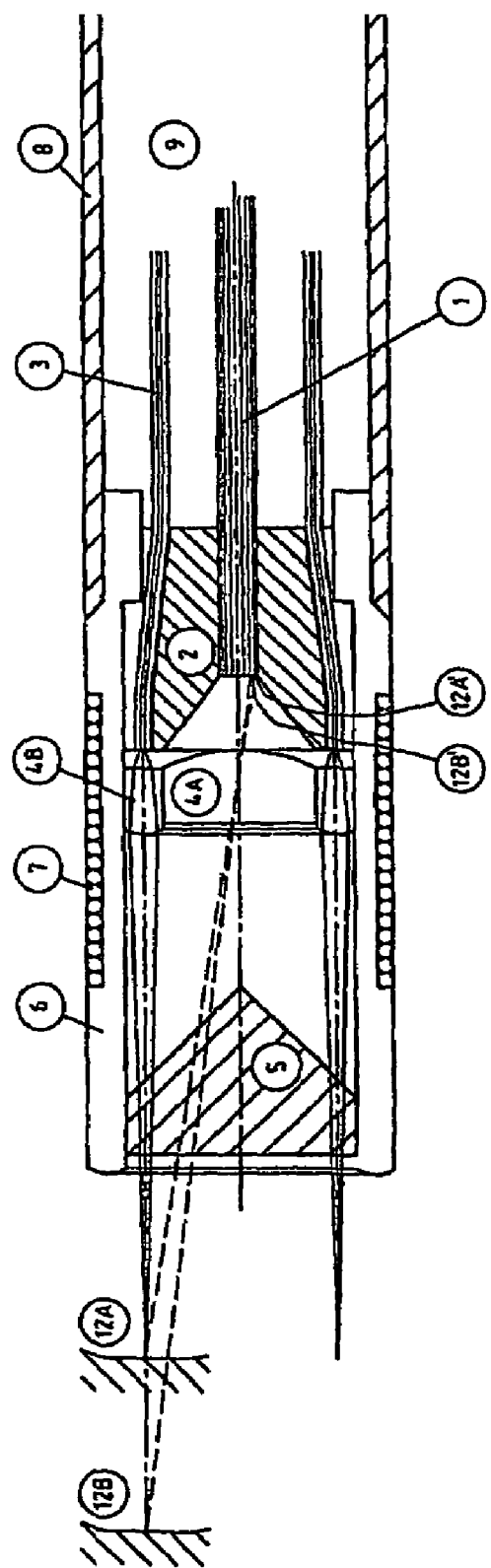
FIG. 2 is a sectional view of the probe in FIG. 1 showing the light path for determining the distance to an object in front of the distal portion of the probe.

In FIG. 2 the light path is shown in a second mode of operation of the probe. The mirror surface 5 is coated with a coating, which in a first wavelength range reflects all light, but which in a second wavelength range transmits all light. The light path of the light in the second wavelength range is shown in FIG. 2. Here light in the second wavelength range emitted from the lens 4B passes through the lens 5 and is reflected from any object 12A, 12B in front of the probe. At 12A and 12B the end wall of the canal is shown at two different distances from the probe. When an ear canal is scanned the tympanic membrane is the end of the canal. The reflected light is also transmitted right through mirror element 5 and through lens 4A and forms an image of the area in front of the probe on the surface of image guide 1. At the proximal end of the image guide the two pictures, namely the front and the circumferential picture, are either led to each their CCD element by the use of a further semitransparent mirror, or led to one and the same CCD element which is chosen so as to be selectively sensitive to the two wavelength ranges.

Using a colour sensitive CCD element has the further advantage that colour information may be used when analyzing the light reflected from the surface of an ear canal. If white light is used, it is possible to determine the relative content of red, green and blue light in the received signal, and thereby foreign objects such as earwax may be identified. This is because earwax will reflect the light in other wavelength ranges than the naked skin of the ear canal. If the semitransparent mirror option described above is employed this will cause some restrictions as to how detailed the colour information is, as only a limited range of wavelengths may be reflected from the mirror surface 5. In the generated data model any lump of earwax may be left out, and the data for the particular surface of the ear canal may be generated through extrapolation using the data from the surrounding wall parts.

The semitransparent mirror surface 5 provides another possibility, namely that a conventional picture is captured through this mirror. This is done by using the image guide in the same fashion as in usual endoscobes. Here light in the wavelength range in which the mirror surface is transparent is guided through the image guide from the proximal end thereof to the tip of the probe. Reflected light is transmitted back through the image guide and by means of a beamsplitter directed towards the surface of a CCD. Thereby the CCD may capture a natural image of the objects in front of the probe, and such an image could be valuable for the person conducting an ear scan.

In FIGS. 1 and 2 a coil 7 is shown at the tip of the probe. The coil is used to generate a magnetic field, which is picked up by sensors shown schematically in FIG. 3. At each sensor position A, B and C two ore more sensors are located, which are designed to register the magnetic field in each their direction. Through this arrangement the exact location and orientation of the tip of the probe can be determined at any time. In the case shown in FIG. 3, the probe is located inside the canal of a human ear, shown schematically in the figure. The three sensor locations are arranged in a fixed construction, which in use is held immobilized relative to the patient's head. In the embodiment shown in FIG. 3, the fixed construction comprises a tripod, whereby each of the sensor positions are placed at the outer end of each of the branches of the tripod. In use the coil 7 at the probe tip is driven at a fixed frequency and by using a lock-in procedure, any noise coming from other magnetic fields in the surroundings may be cancelled out from the sensor signals.

In the described embodiment only one coil is located at the tip of the probe, and the coil is aligned with the length axis of the probe. This means that rotational movement of the probe about its length axis cannot be detected by measuring the magnetic field. It is suggested according to the invention, that the probe is made rotationally rigid, so that if the proximal end of the probe is retained and prevented from rotation about the length axis, then the distal end cannot rotate either. In this way only three different position and two different rotational parameters must be obtained to fully locate the probe in the canal.

Figure 3:
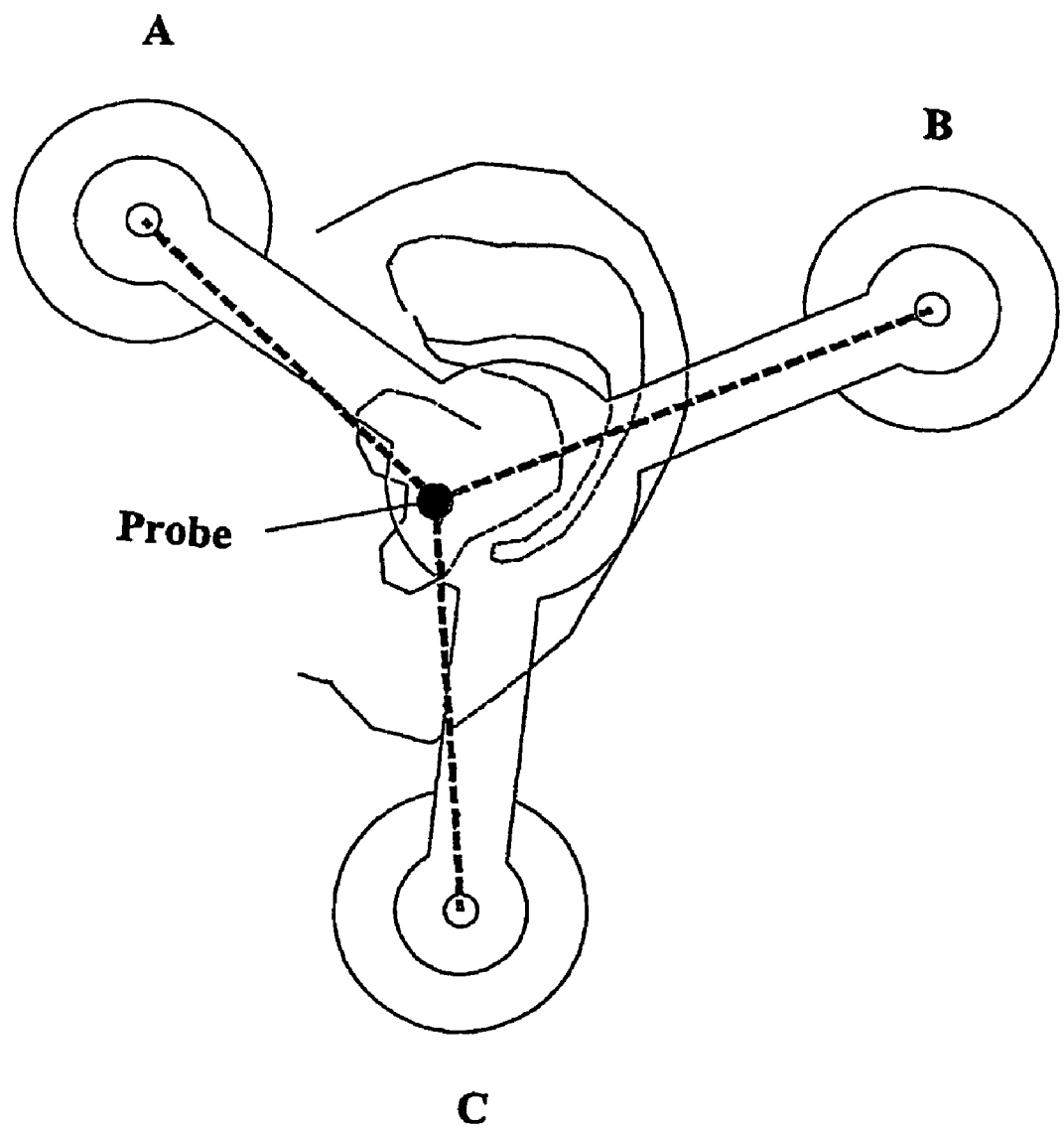
FIG. 3 is a side view showing the human ear and the arrangement of the position sensors.

A guiding arrangement for the probe may be located at the tripod shown in FIG. 3. A guiding arrangement may comprise two or more opposite flat rollers between which the probe is to pass. By slightly squeezing the probe between the rollers, rotational movement of the probe around the length direction is prevented. Such a guiding mechanism may however be implemented in many different ways.

In use the probe is gently inserted into the ear, and the magnetic sensors are placed in close relation to the patient's head. Placing the probe in the ear is done while objects in front of the probe are monitored as described through the semi transparent mirror. A real picture may be obtained, and/or the distance to the tympanic membrane is measured as previously described. The picture captured this way is displayed on a monitor, so that the operator may know when the probe is approaching the tympanic membrane. Once the region near the tympanic membrane is reached, the measurements may commence. This is done while retracting the probe as corresponding values of the distances to the canal wall and the position of the probe are recorded. The recording is continued until the probe reaches the outer regions of the outer ear.

The invention claimed is:

1. A method for locating foreign objects on an internal surface of an ear canal and/or ear, the method comprising the steps of:

inserting a light-emitting distal portion of a probe into the ear canal to a location adjacent a tympanic membrane, directing light from the distal portion of the probe to illuminate at least one point of the internal circumferential surface of the ear and/or ear canal, receiving light reflected from the illuminated surface and directing the received light to at least one light sensitive element to generate an output, analyzing the output with respect to spectral composition of the light received at the light sensitive element and identifying foreign objects based on the spectral composition of the received light, analyzing the output to determine a distance from the probe to the internal surface of the canal at points of the circumference, obtaining position data concerning the spatial position and rotation of the distal end of the probe during motion of the probe from a first location to a second location, generating a data model of the internal surface of the canal on the basis of the retrieved position and distance data, and wherein any foreign object identified is omitted from the data model, and the data for a particular surface of the ear canal is generated through extrapolation using data from the surrounding wall parts.

2. A method as claimed in claim 1, where the at least one light sensitive element comprises an array of light sensitive elements such as CCD elements.

3. A method as claimed in claim 1, where the probe has a flexible part and is capable of bending with bends in the ear canal during the movement of the probe from the first to the second location.

4. An apparatus for locating foreign objects on an internal surface of an ear and/or ear canal, the apparatus comprising,
  a probe having a rod part with a proximal end and a distal portion and comprising at least one light guide and a light source at the proximal end of the light guide,
  a light emitting distal portion insertable into the ear canal and having means for directing light from the distal end of the light guide onto at least one point of an internal circumferential surface area of the ear and/or ear canal,
  means for receiving the light reflected from the internal circumferential surface area, and means for directing the received light to at least one light-sensitive element to generate an output,
  means for analyzing the output with respect to the spectral composition of the light received at the light sensitive element to locate any foreign objects,
  means for analyzing the output to determine a distance from the probe to the internal surface of the canal at points of the circumference during motion of the probe from a first location to a second location, and
  means for obtaining position data concerning spatial position and rotation of the distal end of the probe during motion of the probe from the first location to the second location,
  means for generating a data model of the internal surface of the canal on the basis of the position and distance data, foreign object data being omitted and data for a particular surface of the ear canal being generated through extrapolation using data from surrounding wall parts.

5. An apparatus as claimed in claim 4, wherein means are provided for generating a data model of the internal surface of the canal on the basis of the retrieved position and distance data.

6. An apparatus as claimed in claim 4, wherein the light sensitive element comprises an array of light sensitive elements such as CCD elements.

7. An apparatus as claimed in claim 4, where the means for obtaining position data regarding the probe comprise transmitting means associated with the distal portion of the probe, and receiving means arranged at fixed positions outside the canal.

8. An apparatus as claimed in claim 7, wherein the transmitting means comprise a magnetic field-generating coil, and the receiving means comprise Hall-elements.

9. An apparatus as claimed in claim 6, wherein the probe comprise first light guides for transmitting light from the proximal to the distal end and a first mirror surface for directing the light onto the internal circumferential surface of the canal and a second mirror surface for directing the light reflected from the circumferential surface of the canal towards the CCD element.

10. An apparatus as claimed in claim 6, wherein the light path between the second mirror surface and the CCD further comprise an image guide between the distal end and the proximal end of the probe, and where the CCD element is arranged at the proximal end of the probe, so as to receives the light emitting from the image guide.

11. An apparatus as claimed in claim 6, where the light source generates light containing wavelengths within a first wavelength range and a second wavelength range, and where at least the first mirror surface is arranged on a transparent body, whereby the mirror surface reflects light in the first wavelength range and is transparent to light in the second wavelength range and transmits the light in the second wavelength range and where the light in the second wavelength range is directed to the area in front of the distal portion of the probe, and where light reflected from any objects in this area is directed through the transparent body and guided towards the CCD element.

* * * * *